United States Patent [19]
Carollo et al.

[11] Patent Number: 5,846,185
[45] Date of Patent: Dec. 8, 1998

[54] HIGH RESOLUTION, WIDE FIELD OF VIEW ENDOSCOPIC VIEWING SYSTEM

[76] Inventors: Jerome T. Carollo, 1608 Starling Ct., Carlsbad, Calif. 92008; James E. Melzer, 926 Summer Holly La., Encinitas, Calif. 92024

[21] Appl. No.: 713,887

[22] Filed: Sep. 17, 1996

[51] Int. Cl.⁶ .................................................. A61B 1/04
[52] U.S. Cl. .......................... 600/166; 600/111; 600/130; 600/176; 348/45
[58] Field of Search ................................. 600/160, 162, 600/165, 166, 173, 176, 178, 111, 101, 130; 359/376, 462, 464, 466; 348/45, 42, 47

[56] References Cited

U.S. PATENT DOCUMENTS

| | | |
|---|---|---|
| 828,511 | 8/1906 | Saegmuller . |
| 3,889,662 | 6/1975 | Mitsui . |
| 4,037,921 | 7/1977 | Cox ......................................... 313/524 |
| 4,061,135 | 12/1977 | Widran et al. . |
| 4,395,731 | 7/1983 | Schoolman .............................. 600/111 |
| 4,500,181 | 2/1985 | Takahashi . |
| 4,702,571 | 10/1987 | Barber ..................................... 600/162 |
| 4,830,460 | 5/1989 | Goldenberg ............................. 600/116 |
| 4,862,873 | 9/1989 | Yajima .................................... 600/111 |
| 4,924,853 | 5/1990 | Jones, Jr. et al. . |
| 4,941,457 | 7/1990 | Hasegawa . |
| 5,122,650 | 6/1992 | McKinley . |
| 5,222,482 | 6/1993 | Clark . |
| 5,295,477 | 3/1994 | Janfaza .................................... 600/166 |
| 5,347,990 | 9/1994 | Ebling et al. ............................ 600/182 |
| 5,385,138 | 1/1995 | Berry . |
| 5,396,366 | 3/1995 | Brown et al. . |
| 5,522,789 | 6/1996 | Takahashi ................................ 600/111 |
| 5,603,687 | 2/1997 | Hori ........................................ 600/166 |
| 5,605,532 | 2/1997 | Schermerhorn ......................... 600/169 |
| 5,613,936 | 3/1997 | Czarnek .................................. 600/166 |
| 5,630,784 | 5/1997 | Siegmund ............................... 600/160 |

FOREIGN PATENT DOCUMENTS

404016812 A  1/1992  Japan ..................................... 600/166

OTHER PUBLICATIONS

F.L. Kooi, "Binocular Configurations of a Night–Flight Head–Mounted Display," *Displays*, vol. 14, No. 1, (1993).

*Primary Examiner*—Richard J. Apley
*Assistant Examiner*—Ira R. Hatton
*Attorney, Agent, or Firm*—David G. Beck; Townsend and Townsend and Crew

[57] ABSTRACT

An endoscopic probe for viewing difficult to reach surfaces is provided. The system utilizes a pair of image transmission elements. The first image transmission element passes a low resolution, wide field of view image of the surface to be examined to one eyepiece. The second image transmission element passes a high resolution, narrow field of view image of a portion of the same surface to a second eyepiece. Thus the viewer receives low resolution, wide field of view information in one eye and high resolution, narrow field of view information in the other eye. The overlapped, low resolution information from the wide field-of-view scene is suppressed by the brain, thus resulting in the two images being combined. The combined image contains both the low resolution, wide field-of-view information and the high resolution, narrow field-of-view information. The endoscopic probe may contain one or more illumination sources in order to provide sufficient light intensity for the imaging system.

22 Claims, 5 Drawing Sheets

HIGH RESOLUTION, WIDE FIELD OF VIEW ENDOSCOPIC VIEWING SYSTEM

The present invention relates generally to visual display systems and, more particularly, to an endoscopic viewing system which can be used to direct low resolution, wide field-of-view images of an area under inspection to one eye of a viewer while directing high resolution, narrow field-of-view images of a portion of the same area to the other eye of the viewer.

BACKGROUND OF THE INVENTION

Endoscopes have been in use for a number of years in the medical industry as well as in a variety of other industries. Typically endoscopes use a thin, elongated probe which can be inserted into the area under investigation. Thus endoscopes are useful wherever it is desirable to view an area which would otherwise be unviewable, or at best, difficult to view. For example, a physician can insert an endoscopic probe into a body cavity or organ in order to view the area in question while causing a minimum of tissue damage. Similarly, an engineer can use an endoscopic probe to view an area of a complicated machine without first requiring the disassembly of the machine.

U.S. Pat. No. 4,924,853 discloses an endoscope which provides three-dimensional views of the region in question. The disclosed apparatus uses a pair of transmission elements, such as glass rods, which are mounted side-by-side. The images transmitted by the two elements are passed through a prism system, converted to electrical signals, and used to produce a three-dimensional image on a television monitor.

U.S. Pat. No. 3,889,662 discloses an endoscope which uses two image guiding fiber bundles. One fiber bundle is used to transmit an image from the distal end section of the endoscopic probe while the second fiber bundle is used to transmit an image from a side surface of the distal end section. Both bundles are coupled to a single eyepiece. The images from the two fiber bundles are simultaneously observable from the common eyepiece.

U.S. Pat. No. 5,385,138 discloses a stereoscopic endoscope. The apparatus uses a pair of side-by-side transmission elements which are mounted to a dual prism-eyepiece housing. The system includes an optical fiber which provides illumination from a light source.

From the foregoing, it is apparent that an endoscope which can simultaneously provide both low resolution, wide field of view imagery and high resolution, narrow field of view imagery is desired. This device is of particular interest in the area of micro-surgery in which achieving high resolution while observing a wide field of view is critical.

SUMMARY OF THE INVENTION

The present invention provides an endoscopic probe for viewing difficult to reach surfaces utilizing a pair of image transmission elements. The first image transmission element passes a low resolution, wide field of view image of the surface to be examined to one eyepiece. The second image transmission element passes a high resolution, narrow field of view image of a portion of the same surface to a second eyepiece. When the viewer looks through the pair of eyepieces, the two images are combined.

In one embodiment of the invention, the pair of image transmission elements are individual optical fiber bundles which are housed in a flexible probe. Within the examination or distal end of the probe are two individual objective lens assemblies as well as an outer, protective window. At the viewing end of the probe are two individual collimating lens assemblies leading to the individual eyepieces.

In an alternate embodiment of the invention useful for applications in which it is difficult to sufficiently illuminate the surface to be examined, the endoscopic probe of the invention may be modified to include one or more light transmitting elements. Preferably the light transmitting elements are optical fiber bundles which run parallel to the image transmitting elements throughout the length of the probe. The energy from an illumination source is coupled to one end of the light transmitting element, causing light to exit the opposite or distal end of the element and illuminate the area to be examined.

A further understanding of the nature and advantages of the present invention may be realized by reference to the remaining portions of the specification and the drawings.

DESCRIPTION OF THE PREFERRED EMBODIMENT

Figure 1:
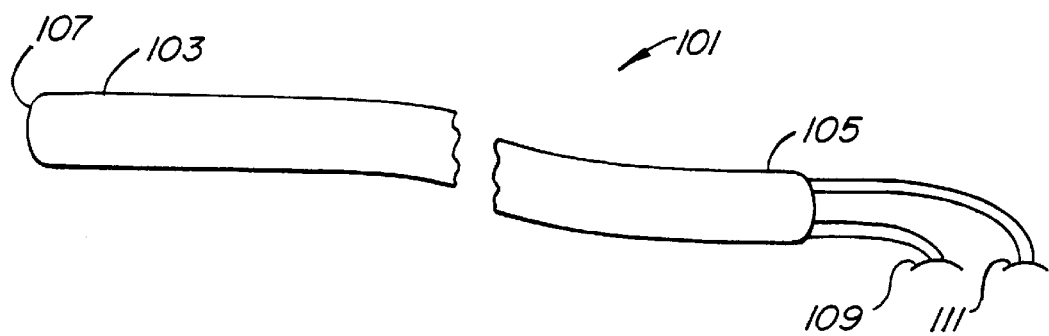
FIG. 1 is an illustration of an outside view of one embodiment of the invention.

FIG. 1 is an illustration of an outside view of one embodiment of the invention. An endoscopic probe 101 has both a distal portion 103 and a viewing portion 105. Distal portion 103 is placed in proximity to the surface to be examined. At the end of distal portion 103 is a window 107. Window 107 protects the internal elements of probe 101 from the environment as well as providing an outer surface which can be easily cleaned, an important feature for probes which are to be used to examine organs during surgery. In this embodiment probe 101 is flexible, thus providing accessibility to a variety of locations. Probe 101 may also be rigid in construction.

Viewing portion 105 is coupled to two eyepieces, 109 and 111. Eyepieces 109 and 111 may be rigidly coupled to a stand (not shown), thus allowing the viewer to easily select between the endoscopic view or an unaided view of the area in question. This embodiment is of particular use to a physician since it allows the physician to monitor both the patient's general condition as well as the particular area under examination. Eyepieces 109 and 111 may also be coupled to a head mounted display (HMD). The HMD (not shown) allows the user additional mobility while still obtaining an endoscopic view of the area of interest. HMD's are well known and therefore a detailed description is unnecessary.

Figure 2:
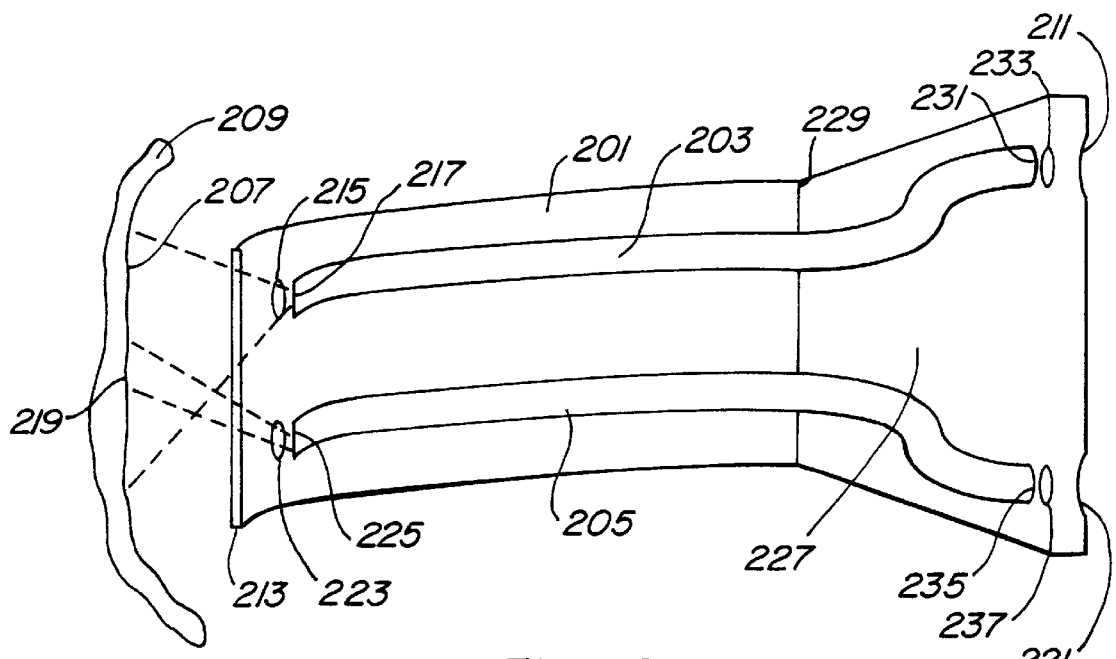
FIG. 2 is a cross section of an embodiment of the invention.

FIG. 2 is a cross section of one embodiment of the invention. In this embodiment an endoscopic probe body 201 contains a first image transmission element 203 and a second image transmission element 205. Although probe body 201 is not necessary for the invention to provide the user with the desired images, it is preferable to provide protection against damage for elements 203 and 205 as well as any other required optical components. Damage may be caused either during cleaning, for example during preparation for a surgical procedure, or during routine use. It is also possible to individually encase elements 203 and 205 and their respective optical components. However, if elements 203 and 205 are individually encased, the distal ends of each of the elements must still be rigidly coupled together to insure that the areas of the examination surface imaged by each element are properly located with respect to one another.

In the preferred embodiment elements 203 and 205 are comprised of optical fiber bundles. Element 203 transmits a low resolution, wide field of view image of an area 207 of a surface 209 to a first eyepiece 211. This image is transmitted through a window 213, an objective lens assembly 215, and focussed on a distal end portion 217 of element 203. Element 205 transmits a high resolution, narrow field of view image of a portion 219 of area 207 to a second eyepiece 221. This image is transmitted through window 213, an objective lens assembly 223, and focussed on a distal end portion 225 of element 205. Thus the viewer receives low resolution, wide field of view information in one eye and high resolution, narrow field of view information in the other eye. The overlapped, low resolution information from the wide field-of-view scene is suppressed by the brain, thus resulting in the two images being combined. The combined image contains both the low resolution, wide field-of-view information and the high resolution, narrow field-of-view information.

In the embodiment of the invention illustrated in FIG. 2, endoscopic probe 201 is coupled to a viewing fixture 227 at a joint 229. Viewing fixture 227 contains eyepieces 211 and 221. The image transmitted by element 203 passes out of a view end portion 231 and through a collimating lens assembly 233 before passing through eyepiece 211. Similarly, the image transmitted by element 205 passes out of a view end portion 235 and through a collimating lens assembly 237 before passing through eyepiece 221. The focal lengths of collimating optical assemblies 233 and 237 are selected so that the image presented to the user via either eye appears to be the same distance from the user. Typically the focal lengths are selected to image the displayed scenes at infinity.

Figure 3:
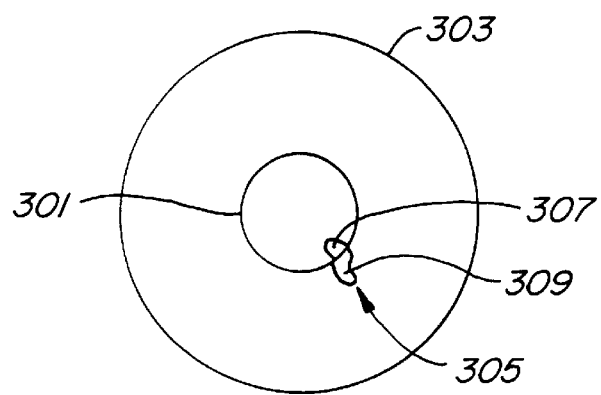
FIG. 3 illustrates the overlap of two images as seen by the viewer.

FIG. 3 is an illustration of two images presented to the user. As illustrated, the high resolution, narrow field of view image 301 presented to one eye of the viewer is a subset of the low resolution, wide field of view image 303 presented to the other eye of the viewer. At a site 305 is a surface feature of the area under examination. A portion 307 of site 305 is within high resolution image 301 while a second portion 309 of site 305 lies outside of high resolution image 301. Since the optical assemblies within the eyepieces are designed to cause the high resolution and low resolution images to coincide, the edge of the surface feature at site 305 appears to be continuous. Thus one eye of the user does not perceive the feature to be of a different size or location than that perceived by the other eye. Since the two images coincide and are of the same magnification, the viewer is able to unconsciously combine them into a single image.

Figure 4:
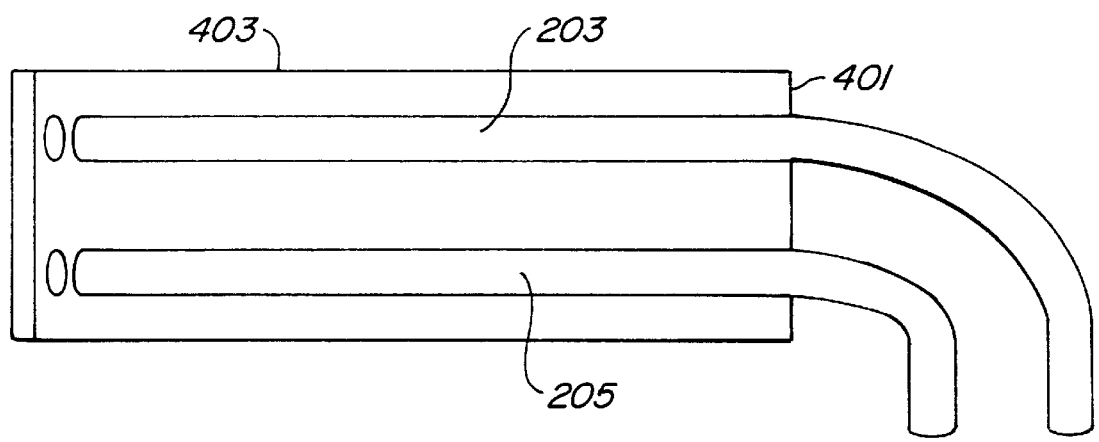
FIG. 4 is an illustration of an embodiment of the invention utilizing an alternate viewing structure.

FIG. 4 is an illustration of an alternate embodiment of the invention. This embodiment is identical to the embodiment illustrated in FIG. 2 except for the viewing structure. In this embodiment optical fiber bundles 203 and 205 extend beyond end 401 of probe 403. The portions of fiber bundles 203 and 205 extending beyond probe 403 can then be attached to a removable HMD system, such as that illustrated in FIG. 5.

Figure 5:
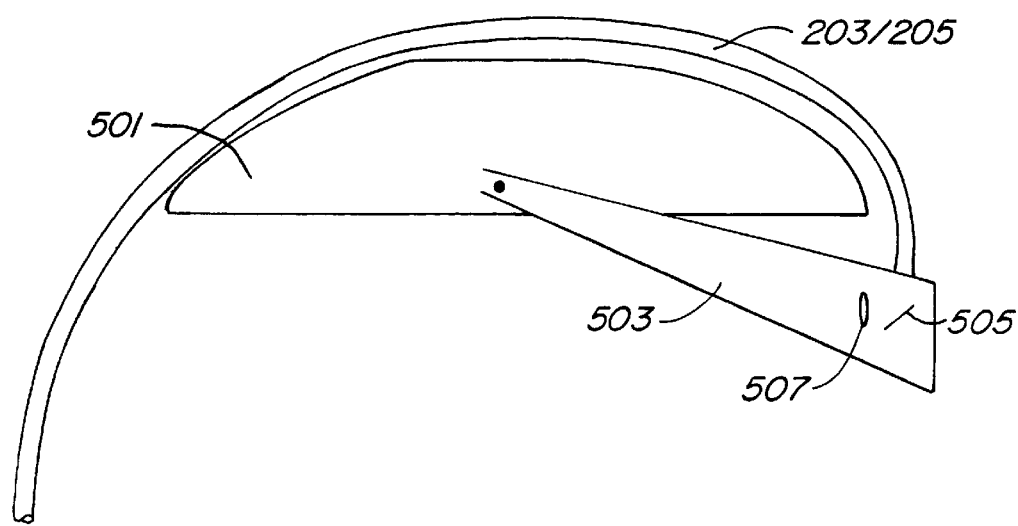
FIG. 5 is an illustration of an HMD system suitable for use with the present invention.

FIG. 5 is an illustration of one HMD system suitable for use with the present invention. In this system optical fiber bundles 203 and 205 are attached to a helmet 501 and an adjustable visor 503. When the visor is placed in a viewing position, as shown, images transmitted by the fiber bundles are reflected by a mirror 505 and passed through a collimating optics assembly 507 to the user.

Figure 6:
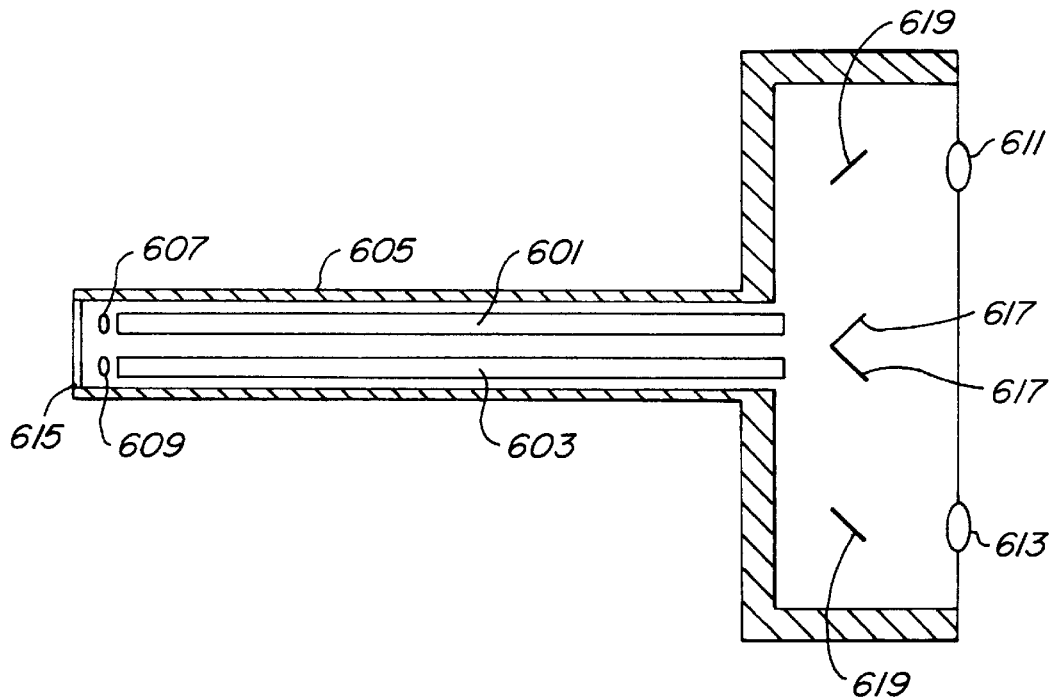
FIG. 6 is an illustration of an embodiment of the invention utilizing glass rods as the image transmission elements.

FIG. 6 is an illustration of an embodiment of the invention utilizing glass rods. This embodiment is similar to that shown in FIGS. 1, 2, and 4 but without the probe flexibility offered by the optical fibers. In this embodiment the image transmission elements are a pair of glass rods, 601 and 603. As in the previous embodiment, this system also includes a probe structure 605, objective lens assemblies 607 and 609, collimating lens/eyepiece assemblies 611 and 613, and window 615. The system also includes first fold mirrors 617 and second fold mirrors 619. Preferably the distance between each fold mirror 617 and matching mirror 619 is adjustable, thus allowing the distance separating lens/eyepiece assemblies 611 and 613 to be adjustable to fit individual viewers.

Figure 7:
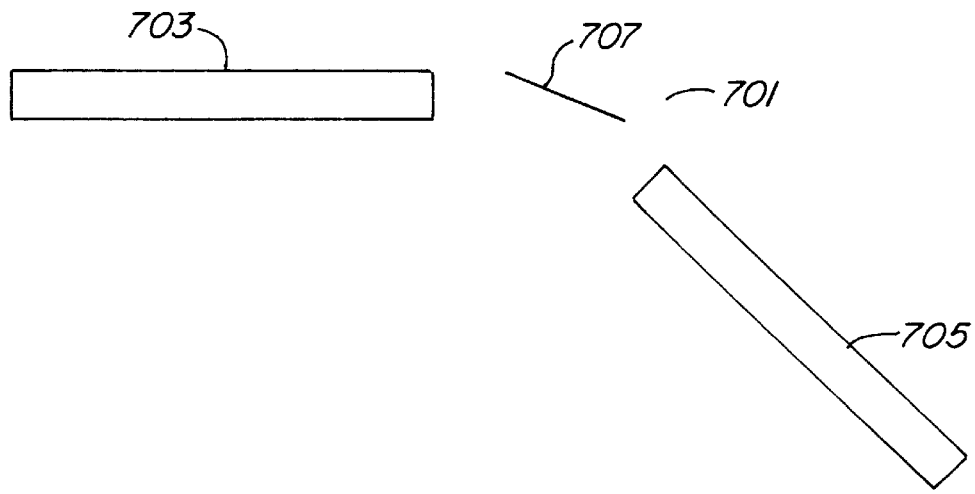
FIG. 7 is an illustration of a flexible image transmission element utilizing two glass rods and a turning mirror.

The embodiment illustrated in FIG. 6 may be given limited flexibility by segmenting glass rods 601 and 603 and adding turning mirrors therebetween as illustrated in FIG. 7. FIG. 7 only shows a single joint 701 between two optical glass rods 703 and 705. However, by using the same technique repeatedly a multi-jointed probe can be fabricated. Within joint 701 is a turning mirror 707. Joint 701 is designed using well known techniques which cause the angle between the optical axis of fiber 703 and mirror 707 to remain equivalent to the angle between the optical axis of fiber 705 and mirror 707 during joint adjustment.

In many applications there is insufficient light at the area to be examined to provide images to the viewer. For these applications a separate light source is necessary. The separate light source may either be external to the endoscopic probe, for example a separate optical fiber, or the endoscopic probe of the invention may be altered to include at least one light source.

Figure 8:
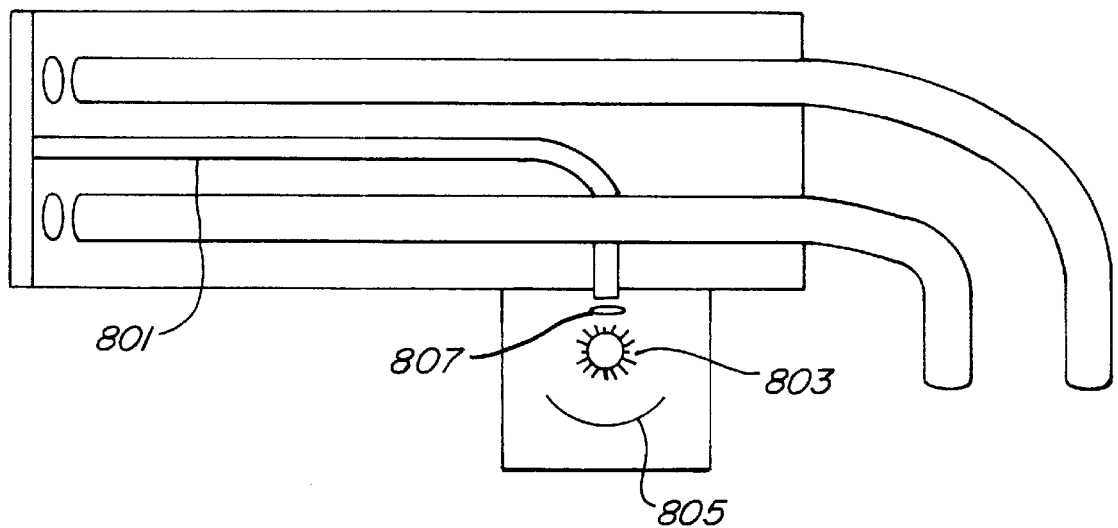
FIG. 8 is an embodiment of the invention which includes an illumination source.

FIG. 8 is an alternate embodiment of the endoscopic system illustrated in FIG. 4. This embodiment includes the elements contained in FIG. 4 as well as a light transmission element 801. Preferably, light transmission element 801 is designed to match the image transmission elements of the probe. Therefore if the probe uses optical fibers, element 801 is preferably an optical fiber. Similarly, if the probe utilizes glass rods, element 801 is preferably a glass rod. The number of light transmission elements is determined by the amount of light necessary at the surface to be investigated.

In the embodiment of the invention illustrated in FIG. 8, light transmission element 801 is coupled to a light source 803. Preferably light source 803 also includes a reflective optical element 805 and a lens assembly 807 to maximize the amount of light coupled to element 801.

Figure 9:
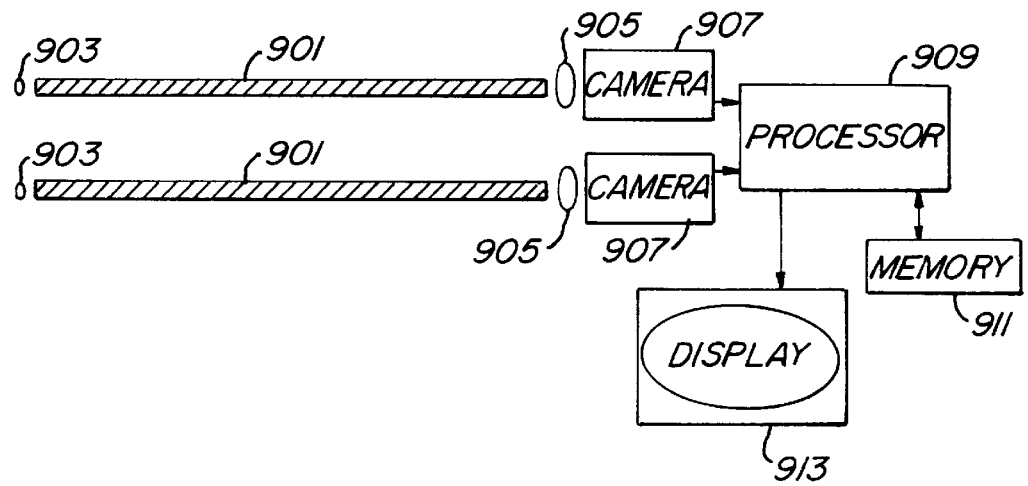
FIG. 9 is an embodiment of the invention which includes a processor and a display.

FIG. 9 is an alternate embodiment of the invention. This embodiment includes optical fibers 901, objective lens assemblies 903, and collimating lens assemblies 905, all of which function in a similar manner to that previously described. In addition, this embodiment of the invention includes digital cameras 907, one receiving a low resolution, wide field of view image and the other receiving a high resolution, narrow field of view image. In this embodiment the digitized images are sent to a processor 909. Preferably processor 909 includes a memory 911 for image storage. Memory 911 allows the image to be stored for later retrieval and manipulation.

Processor 909 combines the two digitized images and presents the combined images on a display 913. Thus the viewer sees a wide field of view, low resolution image in which a portion has been replaced with a high resolution image.

Figure 10:
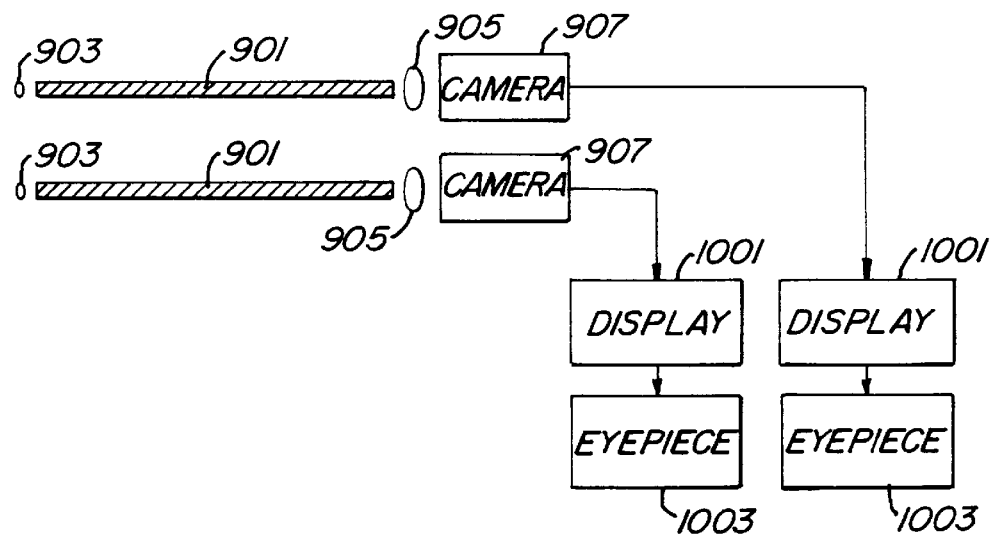
FIG. 10 is an embodiment of the invention which includes a separate digital camera and monitor for each image transmission element.

FIG. 10 is an alternate embodiment of the system shown in FIG. 9. This embodiment includes fibers 901, lens assemblies 903 and 905, and digital cameras 907. In this embodiment each digital camera 907 feeds its respective image to an individual display 1001, for example a liquid crystal display (LCD). Each display 1001 is coupled to an individual viewport or eyepiece 1003. In this embodiment, as in several of the previously described embodiments, the viewer receives low resolution, wide field of view information in one eye and high resolution, narrow field of view information in the other eye. Individual displays 1001 and eyepieces 1003 may be coupled to an HMD (not shown).

Accordingly, the disclosures and descriptions herein are intended to be illustrative, but not limiting, of the scope of the invention which is set forth in the following claims.

We claim:

1. An endoscopic viewing system, comprising:

a probe having a distal end and a viewing end, said distal end terminating at an area to be viewed;

a first image transmission element positioned within said probe and extending from said probe distal end to said probe viewing end, said first image transmission element transmitting a low resolution, wide field of view image of said area to a first eyepiece, said first eyepiece proximate to said probe viewing end; and a second image transmission element positioned within said probe and extending from said probe distal end to said probe viewing end, said second image transmission element transmitting a high resolution, narrow field of view image of a portion of said area to a second eyepiece, said second eyepiece proximate to said probe viewing end.

2. The endoscopic viewing system of claim 1, wherein said probe is flexible.

3. The endoscopic viewing system of claim 1, wherein said first and second image transmission elements comprise optical fiber bundles.

4. The endoscopic viewing system of claim 1, wherein said first and second image transmission elements comprise glass rods.

5. The endoscopic viewing system of claim 1, wherein each of said first and second image transmission elements are comprised of a glass rod assembly and at least one image relay assembly.

6. The endoscopic viewing system of claim 1, further comprising a first lens assembly coupled to said probe distal end of said first image transmission element and a second lens assembly coupled to said probe distal end of said second image transmission element.

7. The endoscopic viewing system of claim 1, further comprising:

a first lens assembly with a first focal length interposed between said first image transmission element and said first eyepiece such that said low resolution, wide field of view image of said area appears to be a first distance away; and a second lens assembly with a second focal length interposed between said second image transmission element and said second eyepiece such that said high resolution, narrow field of view image of said portion of said area appears to be a second distance away, wherein said first distance and said second distance are substantially equivalent.

8. The endoscopic viewing system of claim 1, further comprising at least one illuminating transmission element positioned within said probe, wherein said illuminating transmission element provides illumination of said area to be viewed.

9. The endoscopic viewing system of claim 8, further comprising a light source coupled to said illuminating transmission element.

10. A method of providing a low resolution, wide field of view image of an area in combination with a high resolution, narrow field of view image of a portion of said area, said method comprising the steps of:

providing a probe wherein a first end of said probe terminates at said area and a second end of said probe terminates at a viewing site;

transmitting said low resolution, wide field of view image through a first image transmission element to a first eyepiece, wherein said first image transmission element is positioned within said probe and said first eyepiece is proximate to said viewing site; and transmitting said high resolution, narrow field of view image through a second image transmission element to a second eyepiece, wherein said second image transmission element is positioned within said probe and said second eyepiece is proximate to said viewing site.

11. The method of claim 10, further comprising the step of transmitting illumination from an illumination source to said area.

12. The method of claim 11, wherein said illumination is transmitted through an illumination transmission element.

13. The method of claim 10, further comprising the steps of:

passing said low resolution, wide field of view image through a first lens assembly prior to transmitting said low resolution, wide field of view image through said first image transmission element; and passing said high resolution, narrow field of view image through a second lens assembly prior to transmitting said high resolution, narrow field of view image through said second image transmission element.

14. The method of claim 10, further comprising the steps of:

passing said low resolution, wide field of view image through a first optical collimating assembly, wherein said first optical collimating assembly is prior to said first eyepiece;

passing said high resolution, narrow field of view image through a second optical collimating assembly, wherein said second optical collimating assembly is prior to said second eyepiece; and wherein said low resolution, wide field of view image and said high resolution, narrow field of view image appear equidistant from a user using said first and second eyepieces.

15. An endoscopic viewing system, comprising:

a probe having a distal end and a viewing end, said distal end terminating at an area to be viewed;

a first image transmission element positioned within said probe and extending from said probe distal end to said probe viewing end, said first image transmission element transmitting a low resolution, wide field of view image of said area to a first digital camera; and a second image transmission element positioned within said probe and extending from said probe distal end to said probe viewing end, said second image transmission element transmitting a high resolution, narrow field of view image of a portion of said area to a second digital camera.

16. The endoscopic viewing system of claim 15, further comprising:

a first lens assembly with a first focal length interposed between said first image transmission element and said first digital camera such that said low resolution, wide field of view image of said area appears to be a first distance away; and a second lens assembly with a second focal length interposed between said second image transmission element and said second digital camera such that said high resolution, narrow field of view image of said portion of said area appears to be a second distance away, wherein said first distance and said second distance are substantially equivalent.

17. The endoscopic viewing system of claim 15, wherein said first digital camera outputs a signal representing said low resolution, wide field of view image to a processor and said second digital camera outputs a signal representing said high resolution, narrow field of view image to said processor.

18. The endoscopic viewing system of claim 17, wherein said processor combines said low resolution, wide field of view image with said high resolution, narrow field of view image to form a combined image, wherein said combined image is presented on a display.

19. The endoscopic viewing system of claim 17, wherein a memory is coupled to said processor.

20. The endoscopic viewing system of claim 15, wherein said first digital camera outputs a signal representing said low resolution, wide field of view image to a first display and said second digital camera outputs a signal representing said high resolution, narrow field of view image to second display, wherein said first display is coupled to a first viewing area and said second display is coupled to a second viewing area.

21. The endoscopic viewing system of claim 20, further comprising:

a first lens assembly with a first focal length interposed between said first image transmission element and said first digital camera such that said low resolution, wide field of view image of said area appears to be a first distance away; and a second lens assembly with a second focal length interposed between said second image transmission element and said second digital camera such that said high resolution, narrow field of view image of said portion of said area appears to be a second distance away, wherein said first distance and said second distance are substantially equivalent.

22. The endoscopic viewing system of claim 20, wherein said first and second displays are liquid crystal displays.

* * * * *